(12) United States Patent
Colby

(10) Patent No.: US 9,993,299 B2
(45) Date of Patent: Jun. 12, 2018

(54) SHARPS CONTAINER AND MEDICAL INSTRUMENTS TRAY BRACKET, FASTENER AND SUPPORT SYSTEM

(71) Applicant: Sara M. D. Colby, Morgan Hill, CA (US)

(72) Inventor: Sara M. D. Colby, Morgan Hill, CA (US)

( * ) Notice: Subject to any disclaimer, the term of this patent is extended or adjusted under 35 U.S.C. 154(b) by 540 days.

(21) Appl. No.: 14/214,071

(22) Filed: Mar. 14, 2014

(65) Prior Publication Data

US 2014/0262881 A1    Sep. 18, 2014

Related U.S. Application Data

(60) Provisional application No. 61/798,927, filed on Mar. 15, 2013.

(51) Int. Cl.

| | |
|---|---|
| *B65D 83/10* | (2006.01) |
| *A61B 19/02* | (2006.01) |
| *A61B 50/13* | (2016.01) |
| *A61B 50/36* | (2016.01) |
| A61B 18/02 | (2006.01) |
| A61B 50/15 | (2016.01) |
| A61B 50/20 | (2016.01) |
| A61B 90/50 | (2016.01) |
| A61B 50/33 | (2016.01) |

(52) U.S. Cl.
CPC .......... *A61B 19/0288* (2013.01); *A61B 50/13* (2016.02); *A61B 50/20* (2016.02); *A61B 50/362* (2016.02); *A61B 18/02* (2013.01); A61B 50/33 (2016.02); A61B 2050/155 (2016.02); A61B 2050/21 (2016.02); A61B 2090/504 (2016.02)

(58) Field of Classification Search
CPC ....... A61B 50/362; A61B 50/36; A61B 50/39; A61B 19/0288; A61B 18/02; A61B 2090/504; A61B 2050/155; A61B 2050/21; A61B 2019/0251
USPC ...... 206/363–366, 438, 577, 583; 211/85.13; 220/908, 908.1; 248/125, 312.1, 311.2, 248/318, 323; 604/317, 322
See application file for complete search history.

(56) References Cited

U.S. PATENT DOCUMENTS

| | | | | |
|---|---|---|---|---|
| 4,877,164 A | * | 10/1989 | Baucom ................ | B60N 3/101 16/341 |
| 4,930,631 A | * | 6/1990 | Bruno ................ | A61B 50/362 206/366 |

(Continued)

*Primary Examiner* — Luan K Bui

(57) ABSTRACT

Apparatus and systems herein support sharps containers and medical instruments trays, brackets, fasteners or holders on a mayo cart. Embodiments include an apparatus for attaching to a mayo cart to support a detachably mounted container, bracket or holder. A first portion has an arm extended to approximately the distance from the mayo cart vertical support pole to an outer edge of a mayo cart tray. A second portion attaches to the vertical pole proximate one end of the apparatus. A third portion attaches with the detachable container, bracket or holder proximate the opposite end of the apparatus. Embodiments may also include a detachable container, bracket or holder comprising an attachment portion to receive the third portion of the support apparatus for supportively attaching to the mayo cart. The support apparatus arm may also be extended to an adjustable length for attaching the container, bracket or holder with the mayo cart.

18 Claims, 9 Drawing Sheets

(56) References Cited

U.S. PATENT DOCUMENTS

| | | | | |
|---|---|---|---|---|
| 5,918,739 | A * | 7/1999 | Bilof | A61B 50/362 |
| | | | | 206/366 |
| 5,938,646 | A * | 8/1999 | Carter | A61B 50/36 |
| | | | | 220/524 |
| 5,996,957 | A * | 12/1999 | Kurtz | A47G 23/0225 |
| | | | | 248/231.21 |
| 6,601,813 | B1 * | 8/2003 | Kager | A45D 20/12 |
| | | | | 248/288.31 |
| 7,243,892 | B2 * | 7/2007 | Pfister | F16M 11/04 |
| | | | | 248/281.11 |
| 7,665,606 | B2 * | 2/2010 | Gaillard | A61B 50/10 |
| | | | | 206/363 |
| 9,109,744 | B1 * | 8/2015 | Guerrero | A47G 23/02 |
| 2008/0061195 | A1 * | 3/2008 | Carnevali | F16M 11/14 |
| | | | | 248/125.8 |
| 2009/0127420 | A1 * | 5/2009 | Skaggs | B60N 3/10 |
| | | | | 248/313 |
| 2010/0206757 | A1 * | 8/2010 | Kesselman | A24D 1/02 |
| | | | | 206/494 |

* cited by examiner

SHARPS CONTAINER AND MEDICAL INSTRUMENTS TRAY BRACKET, FASTENER AND SUPPORT SYSTEM

CROSS REFERENCE TO RELATED APPLICATIONS

Pursuant to the provisions of 35 U.S.C. § 119(e), this application claims priority to U.S. Provisional Patent Application Ser. No. 61/798,927, which was filed Mar. 15, 2013, the entire contents of which are incorporated herein by reference.

FIELD OF THE DISCLOSURE

This disclosure relates generally to the field of medical instruments. In particular, the disclosure relates to a sharps container and medical instruments tray or holder bracket, fastener and support system.

BACKGROUND OF THE DISCLOSURE

A typical sharps container for containing medical wastes may be mounted on a wall, or cabinet, or near the base of a mayo cart. One drawback to such an arrangement is that discarding potentially hazardous sharps like needles or blades may require turning away, or bending away from the medical procedure and away from the patient. This procedure for discarding sharps may unnecessarily add potential risks to the medical procedure and/or to the patient. An alternative is to hand off potentially hazardous sharps to an assistant for disposal. This procedure for discarding sharps may unnecessarily add potential risks to the assistant and/or to the practitioner.

To date, more options for securing medical wastes such as sharps and for securing medical instruments have not been fully explored.

BRIEF DESCRIPTION OF THE DRAWINGS

The present invention is illustrated by way of example and not limitation in the figures of the accompanying drawings.

DETAILED DESCRIPTION

The following description discloses apparatus and systems to provide extended support for containers, such as sharps containers, and medical instruments trays, brackets, fasteners or holders on a mayo cart.

Some embodiments disclosed herein include one or more apparatus for attaching to a mayo cart to support a detachably mounted container, bracket or holder. A first portion of such an apparatus may have an arm extended approximately the distance from the mayo cart vertical support pole to an outer edge of a mayo cart tray. A second portion attaches with the vertical pole proximate one end of the apparatus. A third portion attaches with the detachable container, bracket or holder proximate the opposite end of the apparatus. Embodiments may also include a detachable container, bracket or holder comprising an attachment portion to receive the third portion of the support apparatus for supportively attaching the detachable container, bracket or holder to the mayo cart. The support apparatus arm may also be extended to an adjustable length for attaching the container, bracket or holder with the mayo cart.

The apparatus and systems for supporting a detachably mounted container (e.g. a sharps container) bracket or holder as disclosed herein, may permit discarding of potentially hazardous sharps like needles or blades, and not require a practitioner to turn, or bend away from the medical procedure and away from the patient. For example, wherein typical sharps containers for containing medical wastes may be mounted on a wall, or cabinet, or near the base of a mayo cart, embodiments of the apparatus and systems disclosed herein provide extended support for containers, such as sharps containers, instruments trays, brackets, fasteners or holders on the mayo cart, near an outer edge of the mayo cart tray—hence, within easy reach of a practitioner. Thus it becomes unnecessary to turn away, or to bend away from the medical procedure to dispose of potentially hazardous sharps, or to hand off potentially hazardous sharps to an assistant for disposal. Accordingly, some potential risks to medical procedures and/or to the patient, the practitioner, or the assistant may be avoided.

In the following description, numerous specific details such as containers, sharps containers, medical instruments trays, brackets, fasteners, attachment mechanisms, holders, and the like are set forth in order to provide a more thorough understanding of embodiments of the present invention. It will be appreciated, however, by one skilled in the art that the invention may be practiced without such specific details. Additionally, some well known structures, and the like have not been shown in detail to avoid unnecessarily obscuring embodiments of the present invention.

Figure 1:
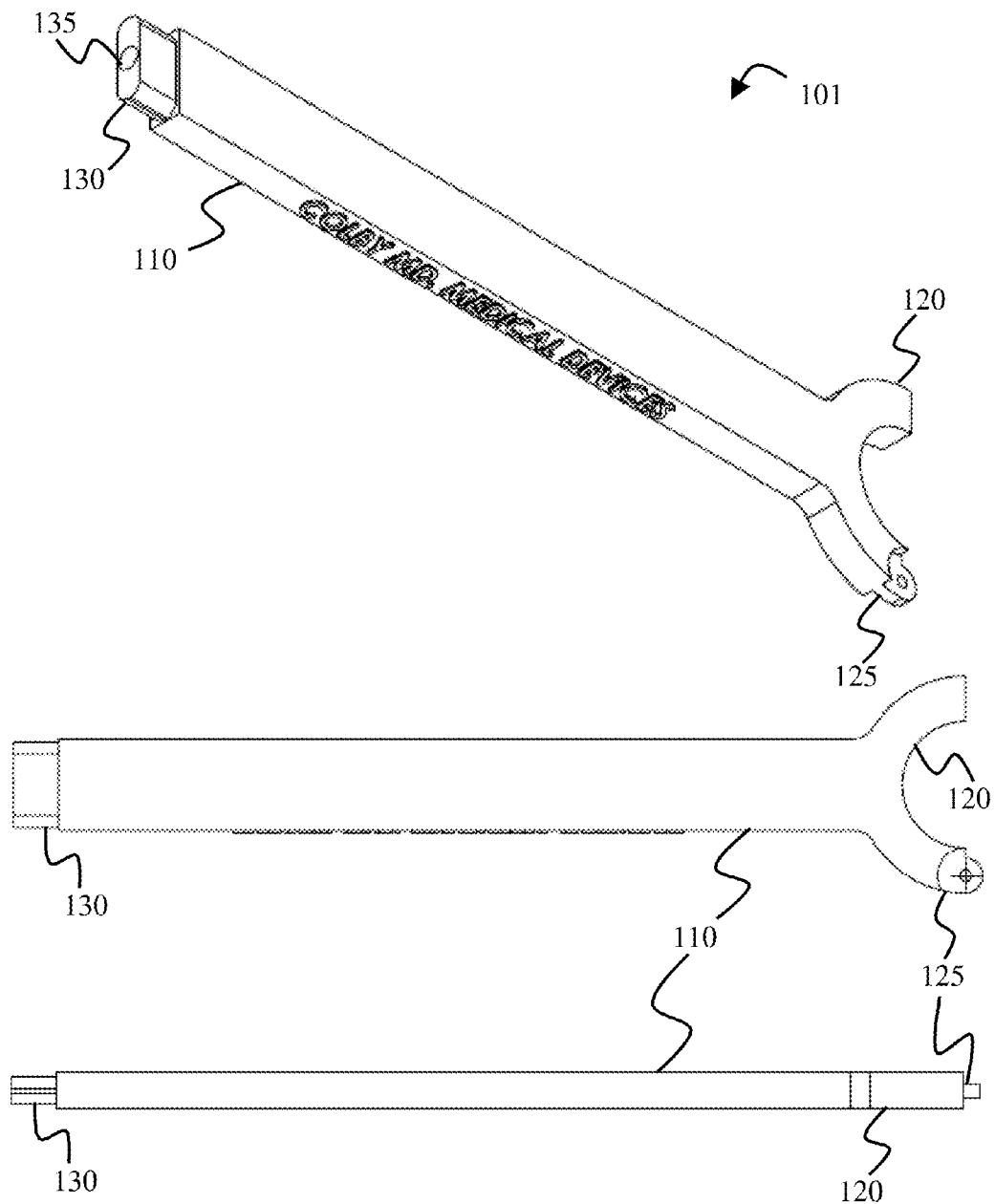
FIG. 1 illustrates one embodiment of a portion of a fastener and support system for a sharps container and medical instruments tray or holder bracket.

FIG. 1 illustrates one embodiment of a portion 101 of a fastener and support system for a sharps container and medical instruments tray or holder bracket. The embodiment includes an apparatus portion 101 for attaching to a mayo cart to support a detachably mounted container, bracket or holder. Apparatus 101 comprises a first portion 110 having an arm extended to a length of approximately a distance from a vertical support pole of a mayo cart to an outer edge of a mayo cart tray. In embodiments of apparatus 101, a first portion 110 may comprise an arm made of aluminum. In alternative embodiments of apparatus 101, a first portion 110 may comprise an arm made of stainless steel, or of carbon fibers, or of plastic, etc. In some alternative embodiments of apparatus 101, a first portion 110 may have an arm operatively extended to an adjustable length, while in others the length may be fixed. Apparatus 101 further comprises a second portion 120 attachable with a securing mechanism, e.g. about an anchor hinge knuckle 125, to secure the apparatus to the vertical pole proximate a first end of the apparatus 101. Apparatus 101 further comprises a third portion 130 to attach with a detachable container, bracket or holder, e.g. using an attachment mechanism 135, proximate a second end and opposite the first end of the apparatus. In one embodiment third portion 130 comprises a rare earth magnet for attachment mechanism 135. In alternative embodiments third portion 130 may comprises a lip, or a cavity for attachment mechanism 135 to attach e.g. with a snap release, or a slide release, or a screw release, of the detachable container, bracket or holder.

Figure 2:
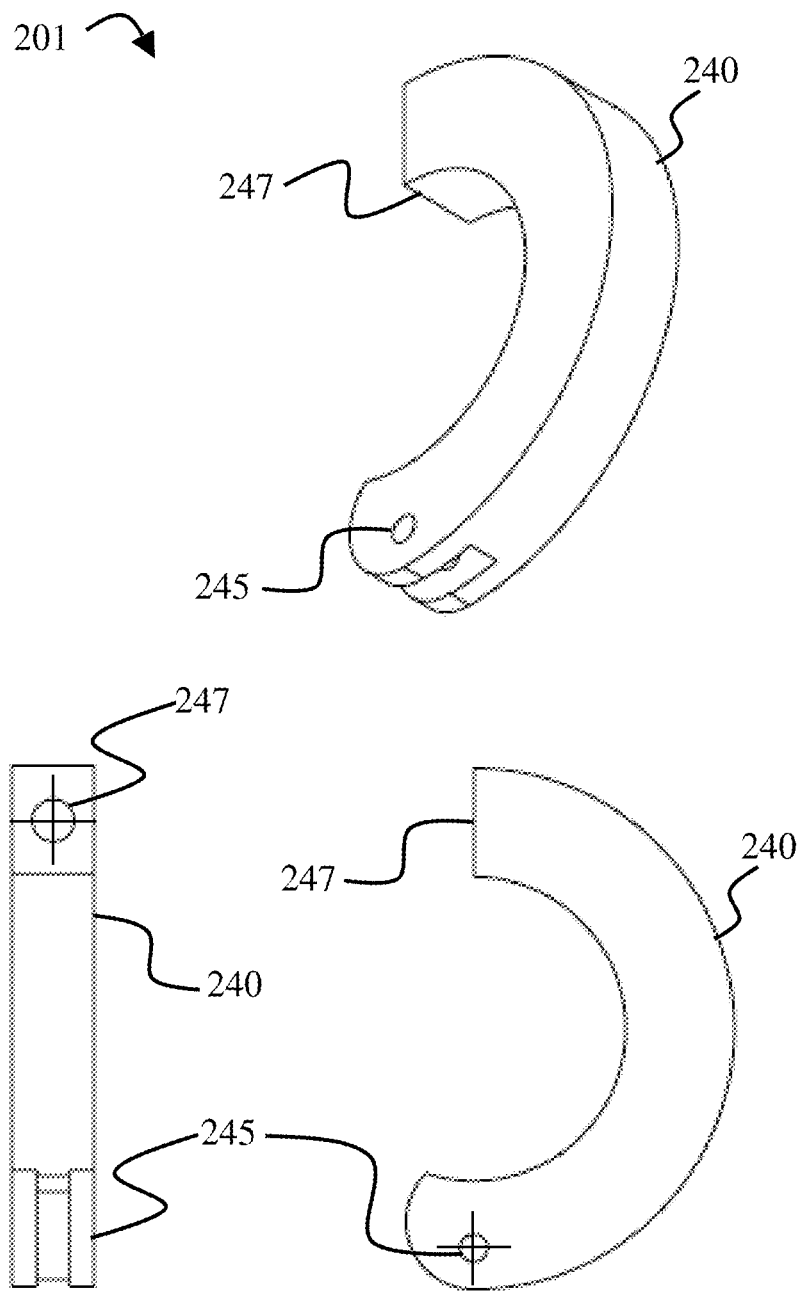
FIG. 2 illustrates an embodiment of another portion of a fastener and support system for a sharps container and medical instruments tray or holder bracket.

FIG. 2 illustrates an embodiment of another portion 201 of a fastener and support system for a sharps container and medical instruments tray or holder bracket. The embodiment includes a securing mechanism portion 201 attachable with the second portion 120 to secure apparatus 101 to the vertical pole of a mayo cart proximate the first end of apparatus 101 to support a detachably mounted container, bracket or holder. Some embodiments of securing mechanism 201 comprise a fourth portion 240 having an outside radius and an inside radius, wherein the inside radius is approximately the same as the vertical pole of a mayo cart. Securing mechanism 201 has one or more hinge knuckle 245, at one end of the fourth portion 240, attachable with the second portion 120, e.g. about the anchor hinge knuckle 125. Securing mechanism 201 also has one or more tightening mechanism 247, at the other end of the fourth portion 240, attachable with the second portion 120. In one embodiment tightening mechanism 247 may hold a bolt or screw, or may receive a bolt or screw for tightening the fourth portion 240 against the second portion 120 and about the vertical pole of a mayo cart. In alternative embodiments tightening mechanism 247 may employ some other means for tightening the fourth portion 240 against the second portion 120 and about the vertical pole of a mayo cart.

Figure 3:
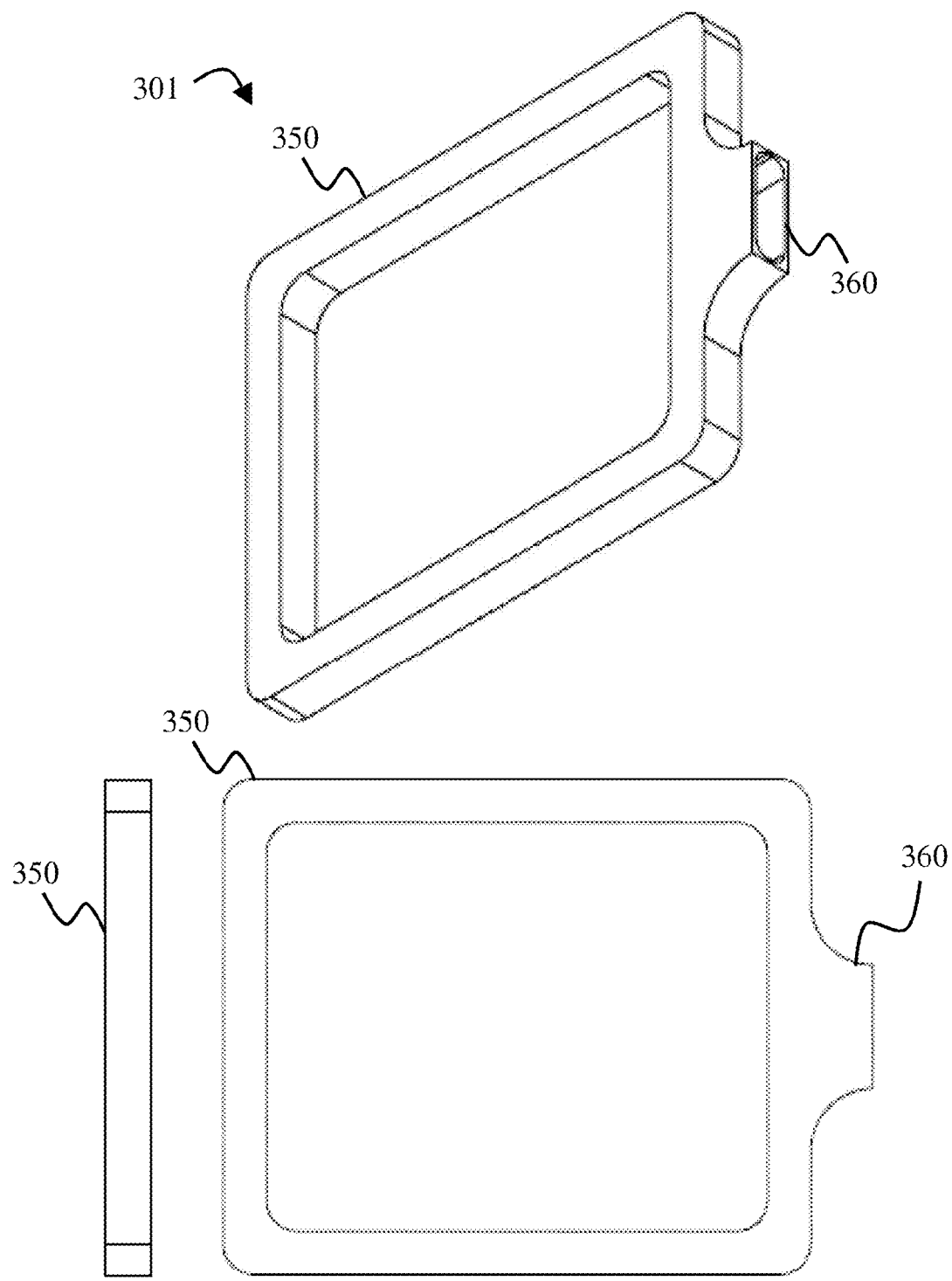
FIG. 3 illustrates an embodiment of another portion of a fastener and support system for a sharps container and medical instruments tray or holder bracket.

FIG. 3 illustrates an embodiment of another portion 301 of a fastener and support system for a sharps container and medical instruments tray or holder bracket. The embodiment of portion 301 includes a detachable holder bracket 350 attachable with the third portion 130 proximate the second end of the apparatus 101, e.g. using a cavity attachment portion 360 to receive the third portion 130 and attachment mechanism 135 to secure with a snap release, or a slide release, or a screw release. In some embodiments, the attachment portion 360 may be made of stainless steel, or of aluminum, or of molded plastic, etc. In some embodiments, the attachment portion 360 may also comprise a ferromagnetic material or a rare earth magnet. In some alternative embodiments, the attachment portion 360 may comprise a snap release, or a slide release, or a screw release, etc. In alternative embodiments, the attachment portion 360 may comprise a cavity to receive a spring release pin, or a pressure release pin to detachably attach, e.g. with the third portion 130 of apparatus 101.

Figure 4:
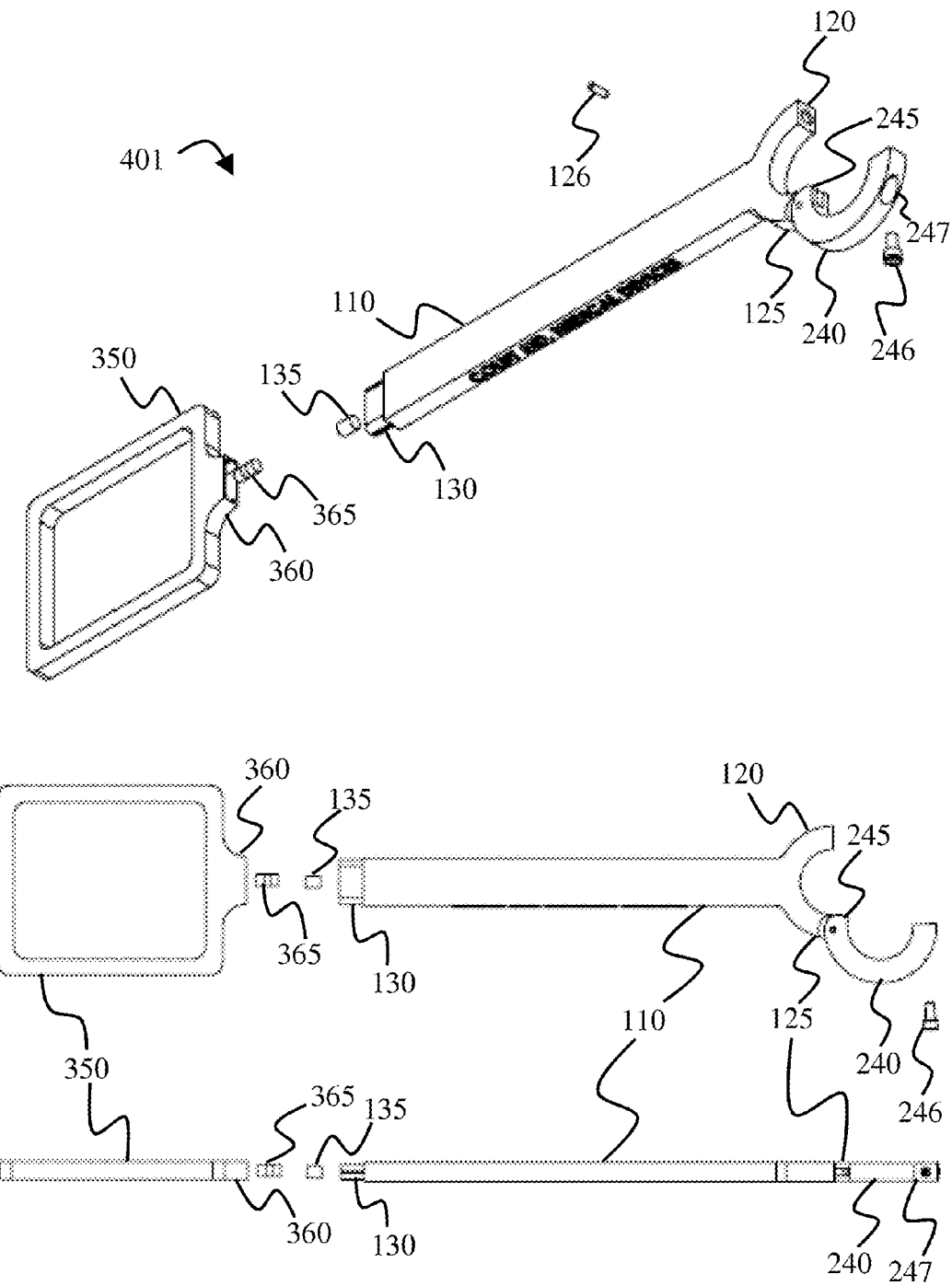
FIG. 4 illustrates an embodiment of a fastener and support system for a sharps container and medical instruments tray or holder bracket.

FIG. 4 illustrates an embodiment of a fastener and support system 401 for a sharps container and medical instruments tray or holder bracket. The embodiment includes a system 401 for attaching, to a mayo cart, a detachably mounted holder bracket 350. System 401 comprises a support apparatus first portion 110 having an arm extended to a length of approximately a distance from the vertical support pole of a mayo cart to an outer edge of a mayo cart tray, with an attachment third portion 130 to attach to a detachable container, bracket or holder proximate a first end and opposite an end attached with the vertical support pole of the mayo cart. In the example illustrated, system 401 further comprises a detachable holder bracket 350 for a sharps container, the holder bracket 350 having an attachment portion 360 to receive the attachment third portion 130 of the support apparatus.

In embodiments of system 401, a support apparatus first portion 110 may comprise an arm made of aluminum. In alternative embodiments of system 401, a support apparatus first portion 110 may comprise an arm made of stainless steel, or of carbon fibers, or of plastic, etc. In some alternative embodiments of system 401, a support apparatus first portion 110 may have an arm operatively extended to an adjustable length, while in others the length may be fixed. In system 401, the attachment third portion 130 is to attach with the detachable holder bracket 350 using an attachment mechanism 135. In one embodiment the attachment third portion 130 comprises a rare earth magnet for attachment mechanism 135. In alternative embodiments the attachment third portion 130 may comprise a lip, or a cavity for attachment mechanism 135 to attach e.g. with a snap release, or a slide release, or a screw release, of a detachable container, bracket or holder. In some alternative embodiments the attachment third portion 130 may comprises a spring release pin, or a pressure release pin to detachably attach, e.g. with the attachment portion 360.

In some embodiments of system 401, the attachment portion 360 of holder bracket 350 may be made of stainless steel, or of aluminum, or of molded plastic, etc. In some embodiments, the attachment portion 360 may also comprise a ferromagnetic material 365 and/or a rare earth magnet. In some alternative embodiments, the attachment portion 360 may also comprise a snap release, or a slide release, or a screw release, etc. In alternative embodiments, the attachment portion 360 may comprise a cavity to receive a spring release pin, or a pressure release pin to detachably attach, e.g. with the attachment third portion 130.

In system 401, the support apparatus further comprises a second portion 120 attachable with a securing mechanism fourth portion 240, e.g. by one or more hinge knuckle 245 about an anchor hinge knuckle 125, to secure the apparatus to the vertical pole proximate a first end of the support apparatus. In one embodiment one or more hinge knuckle 245 may also be threaded to receive a hinge pin 126. Some embodiments of securing mechanism fourth portion 240 have an outside radius and an inside radius, wherein the inside radius is approximately the same as the vertical pole radius of a mayo cart. Securing mechanism fourth portion 240 has one or more hinge knuckle 245 at one end, attachable with the second portion 120 and has one or more tightening mechanism 247 at the other end, attachable with the second portion 120. In one embodiment tightening mechanism 247 may hold a bolt or screw 246, or may receive a bolt or screw 246 for tightening the securing mechanism fourth portion 240 against the second portion 120 and about the vertical pole of a mayo cart. In alternative embodiments tightening mechanism 247 may employ some other means for tightening the fourth portion 240 against the second portion 120 and about the vertical pole of a mayo cart.

Figure 5:
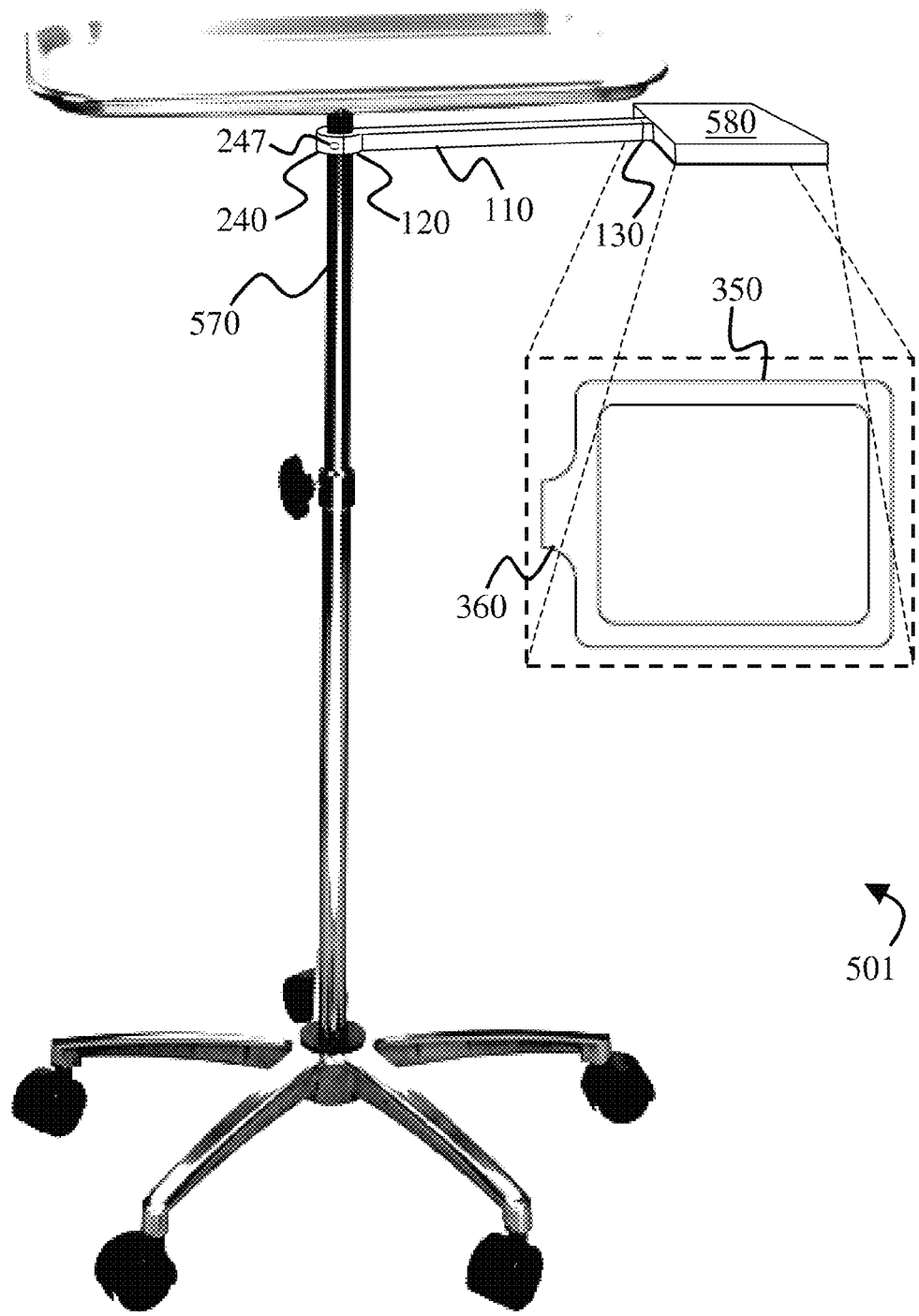
FIG. 5 illustrates an embodiment of a fastener and support system for a sharps container and medical instruments tray or holder bracket on a mayo cart.

FIG. 5 illustrates an embodiment of a fastener and support system 501 for a sharps container and medical instruments tray or holder bracket on a mayo cart. The embodiment includes a system 501 for attaching, to a mayo cart, a detachably mounted bracket 580. System 501 comprises a support apparatus first portion 110 having an arm extended to a length of approximately a distance from the vertical support pole 570 of a mayo cart to an outer edge of a mayo cart tray, with an attachment third portion 130 to attach to a detachable container, bracket or holder proximate a first end and opposite an end attached with the vertical support pole 570 of the mayo cart. In the example illustrated, bracket 580 comprises a detachable holder bracket 350 for a sharps container, the holder bracket 350 having an attachment portion 360 to receive the attachment third portion 130 of the support apparatus.

In embodiments of system 501, a support apparatus first portion 110 may comprise an arm made of aluminum. In alternative embodiments of system 501, a support apparatus first portion 110 may comprise an arm made of stainless steel, or of carbon fibers, or of plastic, etc. In some alternative embodiments of system 501, a support apparatus first portion 110 may have an arm operatively extended to an adjustable length, while in others the length may be fixed. In system 501, the attachment third portion 130 is to attach with the detachable holder bracket 350, e.g. using an attachment mechanism 135. In one embodiment the attachment third portion 130 comprises a rare earth magnet for an attachment mechanism. In alternative embodiments the attachment third portion 130 may comprise a lip, or a cavity for an attachment mechanism to attach e.g. with a snap release, or a slide release, or a screw release, of detachable bracket 580. In some alternative embodiments the attachment third portion 130 may comprises a spring release pin, or a pressure release pin to detachably attach, e.g. with the attachment portion 360.

In some embodiments of system 501, the attachment portion 360 of holder bracket 350 may be made of stainless steel, or of aluminum, or of molded plastic, etc. In some embodiments, the attachment portion 360 may also comprise a ferromagnetic material (e.g. 365) and/or a rare earth magnet. In some alternative embodiments, the attachment portion 360 may also comprise a snap release, or a slide release, or a screw release, etc. In alternative embodiments, the attachment portion 360 may comprise a cavity to receive a spring release pin, or a pressure release pin to detachably attach, e.g. with the attachment third portion 130.

In system 501, the support apparatus further comprises a second portion 120 attachable with a securing mechanism 240 to secure the apparatus to the vertical pole 570 proximate a first end of the support apparatus. Some embodiments of securing mechanism 240 have an outside radius and an inside radius, wherein the inside radius is approximately the same as the vertical pole 570 radius. Securing mechanism 240 has one or more tightening mechanism 247, attachable with the second portion 120. In one embodiment the one or more tightening mechanism 247 may hold one or more bolt or screw (e.g. 246) or may receive one or more bolt or screw for tightening the securing mechanism 240 against the second portion 120 and about the vertical pole 570 of a mayo cart. In alternative embodiments tightening mechanism 247 may employ some other means for tightening the securing mechanism 240 against the second portion 120 and about the vertical pole 570 of a mayo cart.

Figure 6:
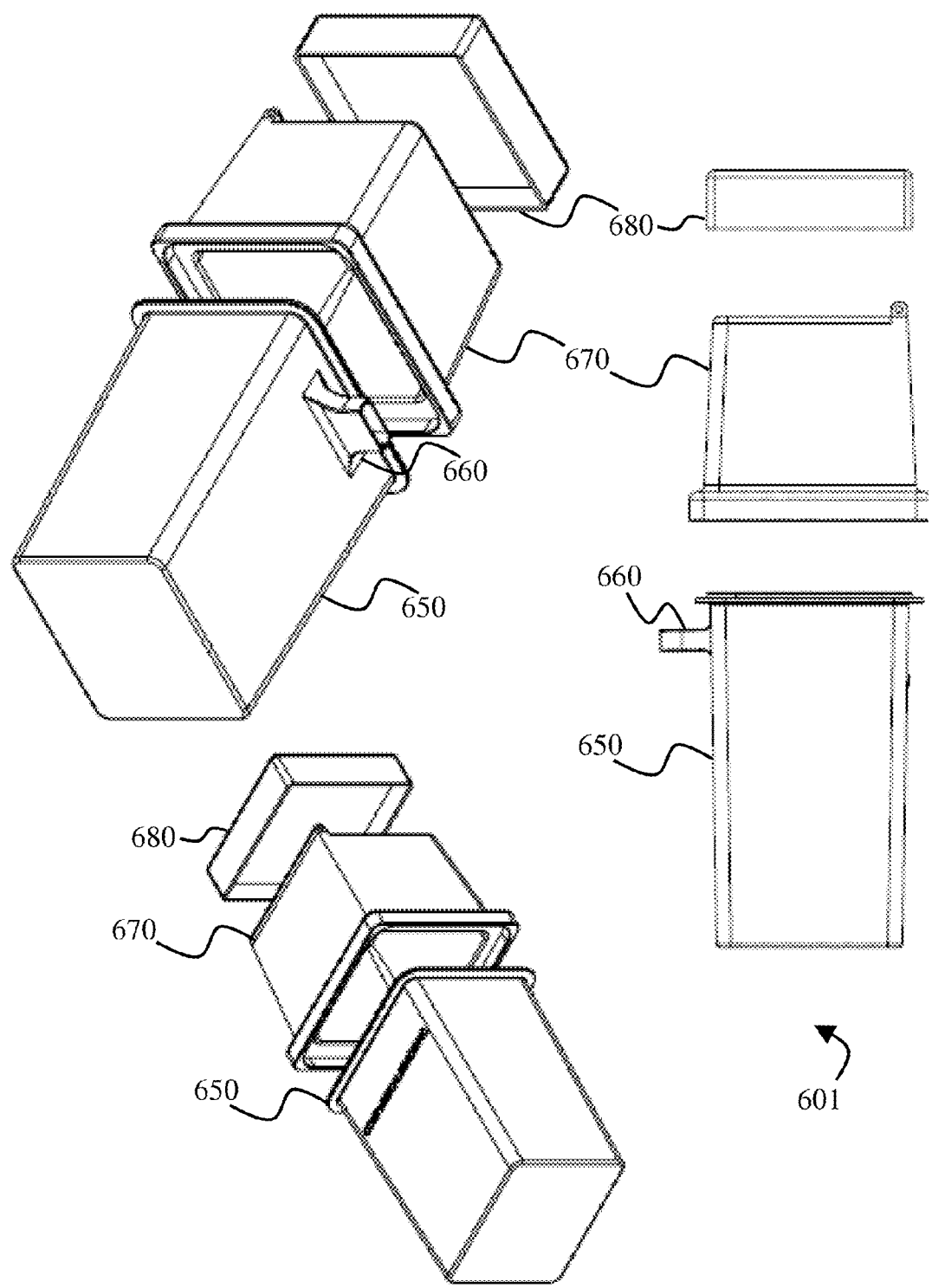
FIG. 6 illustrates an embodiment of another portion of a fastener and support system for a sharps container and medical instruments tray or holder bracket.

FIG. 6 illustrates an embodiment of another portion 601 of a fastener and support system for a sharps container and medical instruments tray or holder bracket. The embodiment includes a sharps container portion 601 comprising a detachable container assembly portion 650 attachable with the attachment third portion 130 of support apparatus 101 for supportively attaching the detachable container assembly portion 650 onto a mayo cart, e.g. using a cavity attachment portion 660 to receive the third portion 130 and attachment mechanism 135 to secure with a snap release, or a slide release, or a screw release. In some embodiments, the attachment portion 660 may be made of stainless steel, or of aluminum, or of molded plastic, etc. In some embodiments, the attachment portion 660 may also comprise a ferromagnetic material 165 and/or a rare earth magnet. In some alternative embodiments, the attachment portion 660 may comprise a snap release, or a slide release, or a screw release, etc. In alternative embodiments, the attachment portion 660 may comprise a cavity to receive a spring release pin, or a pressure release pin to detachably attach, e.g. with the third portion 130 of apparatus 101. Embodiments of sharps container 601 may also comprise a top shell assembly portion 670 securely attachable with the detachable container assembly portion 650, and a closure assembly portion 680. Some embodiments of top shell assembly portion 670 may provide a limited access opening to prevent hands or fingers from entering the sharps container 601. In some embodiments of sharps container 601, the top shell assembly portion 670 is securely attachable with the detachable container assembly portion 650 to prevent sharps container 601 from being intentionally opened or from being accidentally spilled, but the closure assembly portion 680 is pivotally attachable with the top shell assembly portion 670 to permit easy access to sharps container 601 for sharps disposal. In some embodiments, substantial portions of the top shell assembly portion 670, the detachable container assembly portion 650, and the closure assembly portion 680 may be made of molded plastics, e.g. such as polypropylene, etc.

Figure 7:
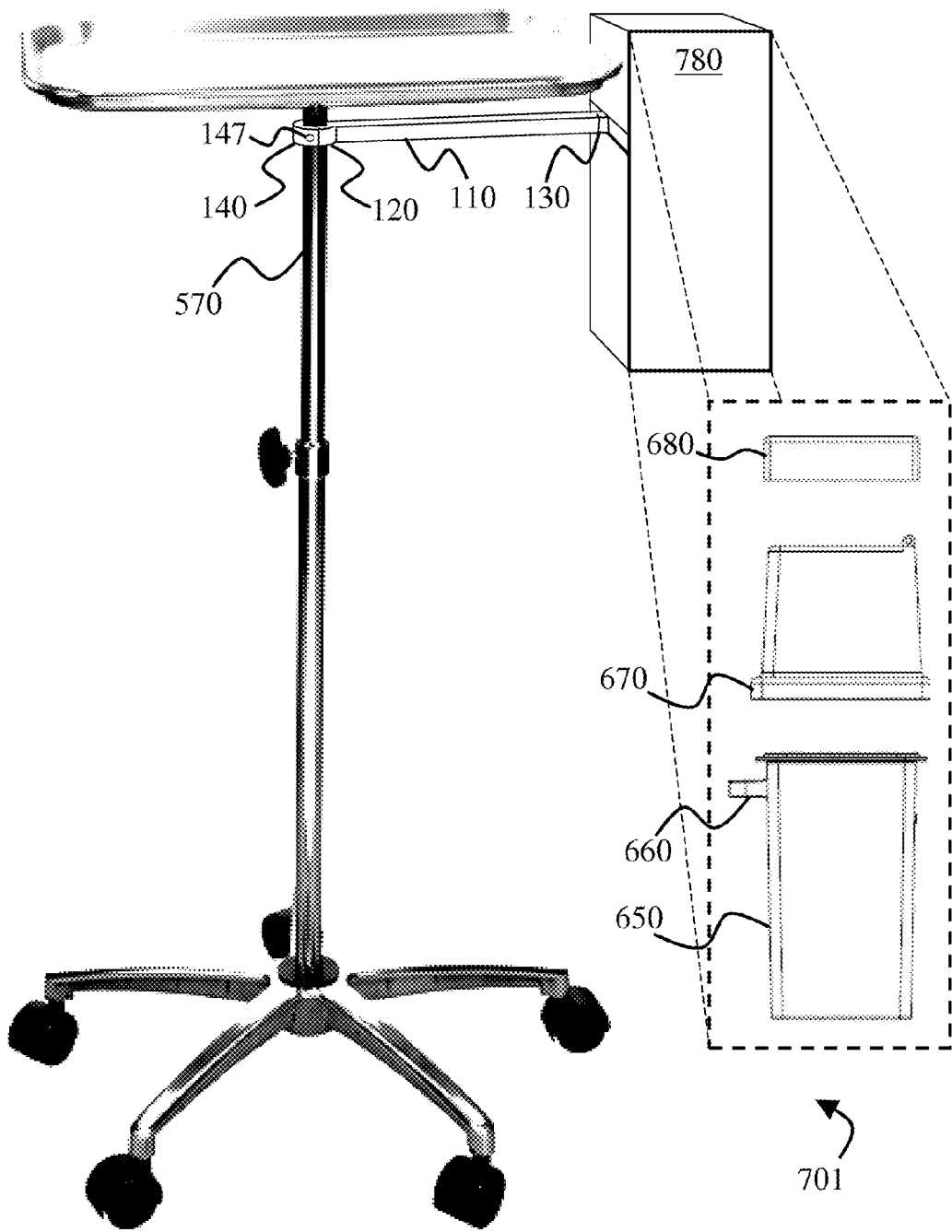
FIG. 7 illustrates another embodiment of a fastener and support system for a sharps container and medical instruments tray or holder bracket on a mayo cart.

FIG. 7 illustrates another embodiment of a fastener and support system 701 for a sharps container and medical instruments tray or holder bracket on a mayo cart. The embodiment includes a system 701 for attaching, to a mayo cart, a detachably mounted detachable container 780. System 701 comprises a support apparatus first portion 110 having an arm extended to a length of approximately a distance from the vertical support pole 570 of a mayo cart to an outer edge of a mayo cart tray, with an attachment third portion 130 to attach to a detachable container, bracket or holder proximate a first end and opposite an end attached with the vertical support pole 570 of the mayo cart. In the example illustrated, detachable container 780 comprises a detachable container assembly portion 650, top shell assembly portion 670, and closure assembly portion 680 for a sharps container, the detachable container assembly portion 650 having an attachment portion 660 to receive the attachment third portion 130 of the support apparatus.

In embodiments of system 701, a support apparatus first portion 110 may comprise an arm made of aluminum. In alternative embodiments of system 701, a support apparatus first portion 110 may comprise an arm made of stainless steel, or of carbon fibers, or of plastic, etc. In some alternative embodiments of system 701, a support apparatus first portion 110 may have an arm operatively extended to an adjustable length, while in others the length may be fixed. In system 701, the attachment third portion 130 is to attach with the detachable container assembly portion 650, e.g. using an attachment mechanism 135. In one embodiment the attachment third portion 130 comprises a rare earth magnet for an attachment mechanism. In alternative embodiments the attachment third portion 130 may comprise a lip, or a cavity for an attachment mechanism to attach e.g. with a snap release, or a slide release, or a screw release, of detachable container 780. In some alternative embodiments the attachment third portion 130 may comprises a spring release pin, or a pressure release pin to detachably attach, e.g. with the attachment portion 660.

In some embodiments of system 701, the attachment portion 660 of container assembly portion 650 may be made of stainless steel, or of aluminum, or of molded plastic, etc. In some embodiments, the attachment portion 660 may also comprise a ferromagnetic material (e.g. 365) and/or a rare earth magnet. In some alternative embodiments, the attachment portion 660 may also comprise a snap release, or a slide release, or a screw release, etc. In alternative embodiments, the attachment portion 660 may comprise a cavity to receive a spring release pin, or a pressure release pin to detachably attach, e.g. with the attachment third portion 130.

In system 701, the support apparatus further comprises a second portion 120 attachable with a securing mechanism 140 to secure the apparatus to the vertical pole 570 proximate a first end of the support apparatus. Some embodiments of securing mechanism 140 have an outside radius and an inside radius, wherein the inside radius is approximately the same as the vertical pole 570 radius. Securing mechanism 140 has one or more tightening mechanism 147, attachable with the second portion 120. In one embodiment the one or more tightening mechanism 147 may hold one or more bolt or screw (e.g. 246) or may receive one or more bolt or screw for tightening the securing mechanism 140 against the second portion 120 and about the vertical pole 570 of a mayo cart. In alternative embodiments tightening mechanism 147 may employ some other means for tightening the securing mechanism 140 against the second portion 120 and about the vertical pole 570 of a mayo cart.

Figure 8:
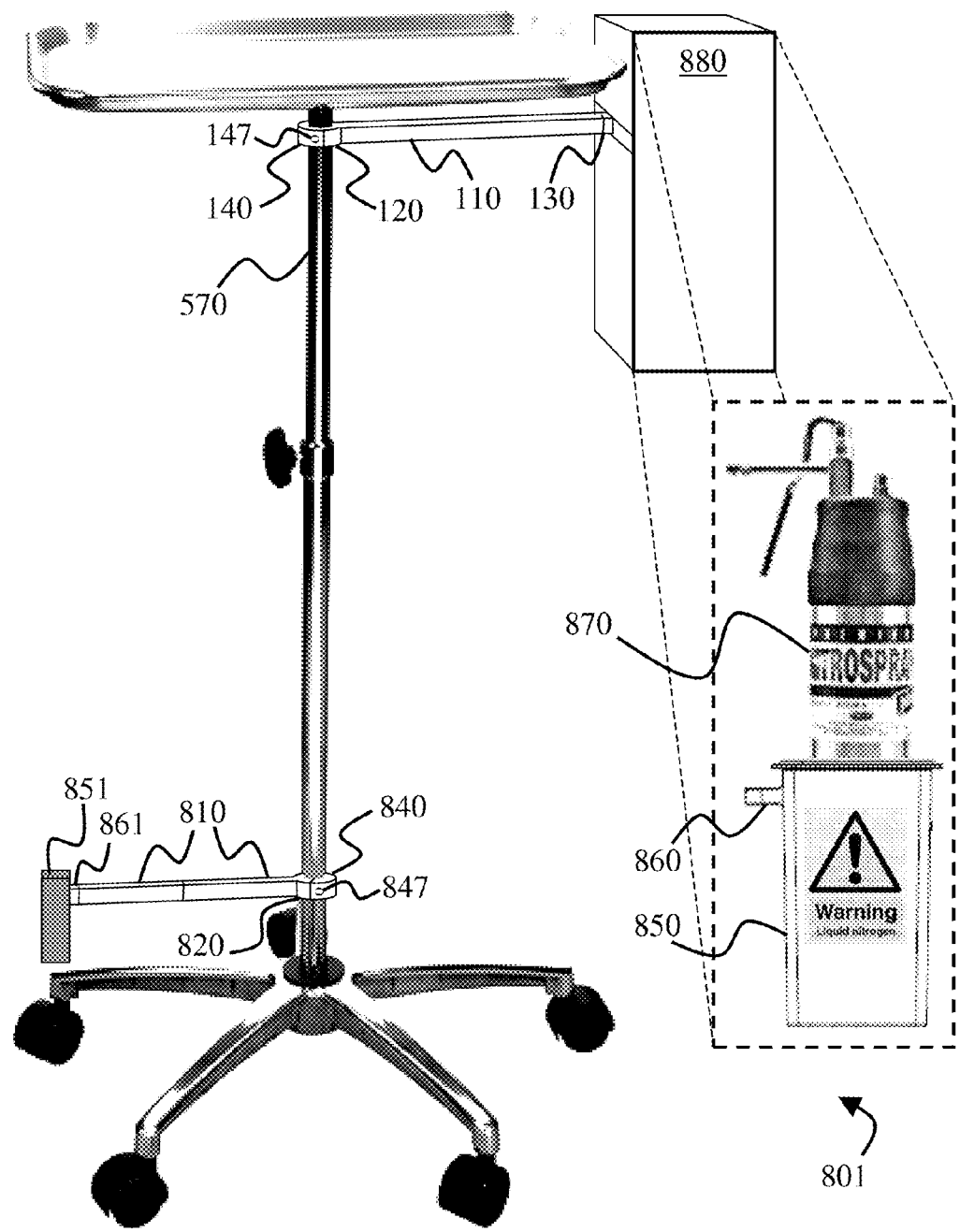
FIG. 8 illustrates another embodiment of a fastener and support system for a medical instruments holder bracket on a mayo cart.

FIG. 8 illustrates another embodiment of a fastener and support system 801 for a medical instruments holder bracket on a mayo cart. The embodiment includes a system 801 for attaching, to a mayo cart, a detachably mounted detachable container 880. System 801 comprises a support apparatus first portion 110 having an arm extended to a length of approximately a distance from the vertical support pole 570 of a mayo cart to an outer edge of a mayo cart tray, with an attachment third portion 130 to attach to a detachable container, bracket or holder proximate a first end and opposite an end attached with the vertical support pole 570 of the mayo cart. In the example illustrated, detachable container 880 comprises a detachable container assembly portion 850 and a liquid nitrogen dispenser 870, the detachable container assembly portion 850 having an attachment portion 860 to receive the attachment third portion 130 of the support apparatus. In alternative embodiments, detachable container 880 may comprise a detachable container assembly portion to hold gloves, or some other items. Embodiments of system 801 may further comprise a support apparatus first portion 810 having an arm extended to a length of approximately a length of a mayo cart leg, with an attachment third portion of the support apparatus to attach to a detachable counterweight 851 opposite an end attached with the vertical support pole 570 of the mayo cart. In the example illustrated, detachable counterweight 851 comprises an attachment portion 861 to receive the attachment third portion of the support apparatus.

In embodiments of system 801, support apparatus first portions 110 and/or 810 may comprise an arm made of aluminum. In alternative embodiments of system 801, a support apparatus first portions 110 and/or 810 may comprise an arm made of stainless steel, or of carbon fibers, or of plastic, etc. In some alternative embodiments of system 801, a support apparatus first portions 110 and/or 810 may have an arm operatively extended to an adjustable length, while in others the length may be fixed. In system 801, the attachment third portion 130 is to attach with the detachable container assembly portion 850, e.g. using an attachment mechanism 135. In one embodiment the attachment third portion 130 comprises a rare earth magnet for an attachment mechanism. In alternative embodiments the attachment third portion 130 may comprise a lip, or a cavity for an attachment mechanism to attach e.g. with a snap release, or a slide release, or a screw release, of detachable container 880. In some alternative embodiments the attachment third portion 130 may comprises a spring release pin, or a pressure release pin to detachably attach, e.g. with the attachment portion 860.

In some embodiments of system 801, the attachment portion 860 of container assembly portion 850 may be made of stainless steel, or of aluminum, or of molded plastic, etc. In some embodiments, the attachment portion 860 may also comprise a ferromagnetic material (e.g. 365) and/or a rare earth magnet. In some alternative embodiments, the attachment portion 860 may also comprise a snap release, or a slide release, or a screw release, etc. In alternative embodiments, the attachment portion 860 may comprise a cavity to receive a spring release pin, or a pressure release pin to detachably attach, e.g. with the attachment third portion 130.

In system 801, the support apparatus further comprises a second portion 120 attachable with a securing mechanism 140 to secure the apparatus to the vertical pole 570 proximate a first end of the support apparatus. Some embodiments of securing mechanism 140 have an outside radius and an inside radius, wherein the inside radius is approximately the same as the vertical pole 570 radius. Embodiments of system 801 may further comprise a second portion 820 attachable with a securing mechanism 840 to secure the apparatus to the vertical pole 570 proximate a first end of the support apparatus. Some embodiments of securing mechanism 840 have an outside radius and an inside radius, wherein the inside radius is approximately the same as the vertical pole 570 base radius. Securing mechanisms 140 and 840 may have one or more tightening mechanism 147 and 847 on one or both ends of each securing mechanism 140 and 847, respectively attachable with the second portions 120 and 820. In one embodiment the one or more tightening mechanisms 147 and 847 may each hold one or more bolt or screw (e.g. 246) or may each receive one or more bolt or screw for tightening the securing mechanisms 140 and 840 against the respective second portions 120 and 820, and about the vertical pole 570 of a mayo cart. In alternative embodiments tightening mechanisms 147 and 847 may employ some other means for tightening the securing mechanism 140 and 840 against the respective second portions 120 and 820, and about the vertical pole 570 of a mayo cart.

Figure 9:
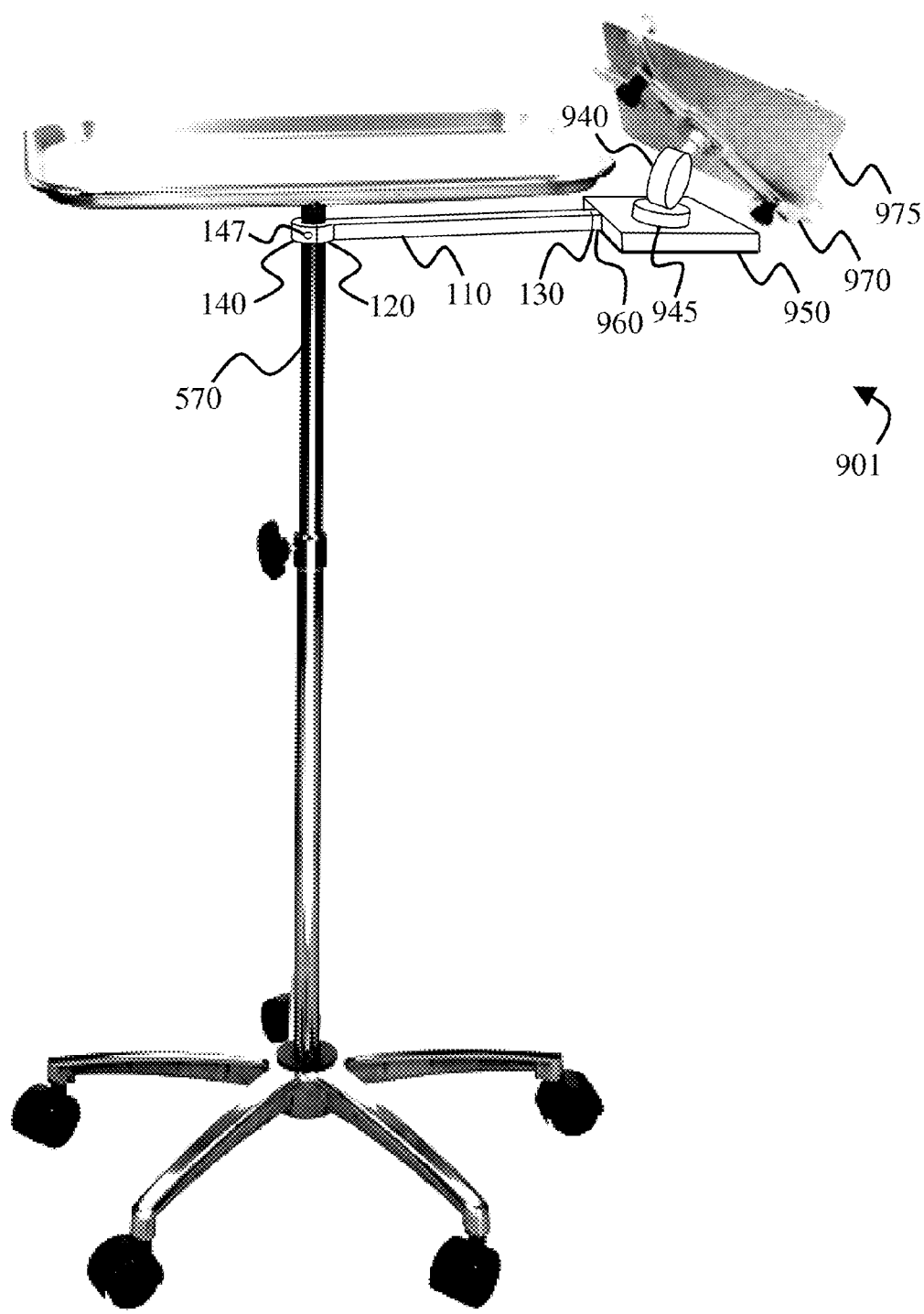
FIG. 9 illustrates another embodiment of a fastener and support system for a medical electronic instruments holder bracket on a mayo cart.

FIG. 9 illustrates another embodiment of a fastener and support system 901 for a medical electronic instruments holder bracket on a mayo cart. The embodiment includes a system 901 for attaching, to a mayo cart, a detachably mounted holder 950. System 901 comprises a support apparatus first portion 110 having an arm extended to a length of approximately a distance from the vertical support pole 570 of a mayo cart to an outer edge of a mayo cart tray, with an attachment third portion 130 to attach to a detachable container, bracket or holder proximate a first end and opposite an end attached with the vertical support pole 570 of the mayo cart. In the example illustrated, holder 950 comprises a detachable instrument holder, e.g. to hold a computing device or an electronic tablet, the holder 950 having an attachment portion 960 to receive the attachment third portion 130 of the support apparatus. In some embodiments the detachably mounted holder 950 may further comprise a vertical (or latitudinal) angular adjuster 940 and a horizontal (or longitudinal) angular adjuster 945 operatively coupled with an angularly adjustable podium 975 and instrument holding clamps 970, e.g. to hold a computing device or an electronic tablet. In alternative embodiments the detachably mounted holder 950 may comprise an instrument holder to hold an electronic surgical control system, an electronic viewing and recording system, a cauterizing device, etc. In other alternative embodiments the detachably mounted holder 950 may comprise a detachable medical tape holder, a detachable paper towel holder, a detachable drawer holder, etc.

In embodiments of system 901, a support apparatus first portion 110 may comprise an arm made of aluminum. In alternative embodiments of system 901, a support apparatus first portion 110 may comprise an arm made of stainless steel, or of carbon fibers, or of plastic, etc. In some alternative embodiments of system 901, a support apparatus first portion 110 may have an arm operatively extended to an adjustable length, while in others the length may be fixed. In system 901, the attachment third portion 130 is to attach with the detachable holder 950, e.g. using an attachment mechanism 135. In one embodiment the attachment third portion 130 comprises a rare earth magnet for an attachment mechanism. In alternative embodiments the attachment third portion 130 may comprise a lip, or a cavity for an attachment mechanism to attach e.g. with a snap release, or a slide release, or a screw release, of detachable holder 950. In some alternative embodiments the attachment third portion 130 may comprises a spring release pin, or a pressure release pin to detachably attach, e.g. with the attachment portion 960.

In some embodiments of system 901, the attachment portion 960 of holder 950 may be made of stainless steel, or of aluminum, or of molded plastic, etc. In some embodiments, the attachment portion 960 may also comprise a ferromagnetic material (e.g. 365) and/or a rare earth magnet. In some alternative embodiments, the attachment portion 960 may also comprise a snap release, or a slide release, or a screw release, etc. In alternative embodiments, the attachment portion 960 may comprise a cavity to receive a spring release pin, or a pressure release pin to detachably attach, e.g. with the attachment third portion 130.

In system 901, the support apparatus further comprises a second portion 120 attachable with a securing mechanism 140 to secure the apparatus to the vertical pole 570 proximate a first end of the support apparatus. Some embodiments of securing mechanism 140 have an outside radius and an inside radius, wherein the inside radius is approximately the same as the vertical pole 570 radius. Securing mechanism 140 has one or more tightening mechanism 147, attachable with the second portion 120. In one embodiment the one or more tightening mechanism 147 may hold one or more bolt or screw (e.g. 246) or may receive one or more bolt or screw for tightening the securing mechanism 140 against the second portion 120 and about the vertical pole 570 of a mayo cart. In alternative embodiments tightening mechanism 147 may employ some other means for tightening the securing mechanism 140 against the second portion 120 and about the vertical pole 570 of a mayo cart.

Apparatus and systems for supporting of a sharps container and medical instruments tray, bracket, fastener or holders on a mayo cart or such are disclosed above. Embodiments include an apparatus 101 for attaching to a mayo cart to support a detachably mounted container, bracket or holder, the apparatus comprising: a first portion 110 having an arm extended to a length of approximately a distance from a vertical support pole of the mayo cart to an outer edge of a mayo cart tray; a second portion 120 attachable with a securing mechanism 201 to secure the apparatus to the vertical pole proximate a first end of the apparatus; and a third portion 130 to attach with a detachable container 780, bracket 580 or holder 950 proximate a second end and opposite the first end of the apparatus. Other embodiments include a detachable container, bracket or holder comprising an attachment portion 360 to receive a first attachment portion 130 of a support apparatus for supportively attaching the detachable container, bracket or holder onto a mayo cart. Embodiments of the support apparatus may have an arm 810 operatively extended to an adjustable length approximately the distance from a vertical support pole of the mayo cart to an outer edge of the mayo cart tray, with an attachment portion to attach to the detachable container, bracket or holder proximate an end of the support apparatus opposite from the end attaching the support apparatus with a vertical support pole of the mayo cart.

Apparatus and systems for supporting a detachably mounted container, bracket or holder as disclosed herein, may permit discarding potentially hazardous sharps like needles or blades, without requiring a practitioner to turn, or bend away from the medical procedure and away from the patient. The apparatus and systems disclosed herein provide extended support for containers, such as sharps containers, instruments trays, brackets, fasteners or holders on the mayo cart near an outer edge of the mayo cart tray and within easy reach of a practitioner. As such, it becomes unnecessary to turn away, or to bend away from the medical procedure to dispose of potentially hazardous sharps, or to hand off potentially hazardous sharps to an assistant for disposal. Accordingly, some potential risks to the medical procedure and/or to the patient, the practitioner, or the assistant may be avoided.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art upon studying this disclosure. Thus, the disclosed embodiments may be readily modifiable in arrangement and detail without departing from the principles of the present disclosure or the scope of the accompanying claims.

What is claimed is:

1. An apparatus and a mayo cart, said mayo cart including a vertical support pole and a mayo cart tray having an outer edge of the mayo cart tray which is not adjacent to the vertical support pole, to support a detachably mounted container, bracket or holder, the apparatus comprising:
    a first portion having an arm extended from the vertical support pole of the mayo cart to the outer edge of the mayo cart tray;
    a second portion attachable with a securing mechanisms to secure the apparatus to the vertical support pole proximate a first end of the apparatus;
    a third portion to attach with a detachable container, bracket or holder proximate a second end and opposite the first end of the apparatus; and
    a portion of a detachable container assembly, the detachable container assembly portion having an attachment portion to receive the third portion of the apparatus.

2. The apparatus of claim 1, the detachable container assembly to hold medical sharps.

3. The apparatus of claim 1, the detachable container assembly to hold a liquid nitrogen dispenser.

4. The apparatus of claim 1, the first portion arm operatively extended to an adjustable length.

5. The apparatus of claim 1, wherein a distance from the vertical support pole of the mayo cart to the outer edge of the mayo cart tray is approximately half the length of the mayo cart tray.

6. The apparatus of claim 1, wherein a distance from the vertical support pole of the mayo cart to the outer edge of the mayo cart tray is approximately half the width of the mayo cart tray.

7. The apparatus of claim 1, wherein a distance from the vertical support pole of the mayo cart to the outer edge of the mayo cart tray is approximately the width of the mayo cart tray.

8. The apparatus of claim 1, the third portion of the apparatus comprising:
   a rare earth magnet.

9. The apparatus of claim 1, the third portion of the apparatus comprising:
   a lip to attach with a snap release of the attachment portion of the detachable container assembly portion.

10. The apparatus of claim 1, the third portion of the apparatus comprising:
    a cavity to attach with a snap release of the attachment portion of the detachable container assembly portion.

11. The apparatus of claim 1, the third portion of the apparatus comprising:
    a cavity to attach with a screw release of the attachment portion of the detachable container assembly portion.

12. The apparatus of claim 1, wherein the third portion of the apparatus is to attach with a molded plastic attachment portion of the detachable container assembly portion.

13. The apparatus of claim 1, the third portion of the apparatus comprising:
    a spring release pin to attach with an attachment portion of the detachable container assembly portion.

14. A system and a mayo cart, said mayo cart including a vertical support pole and a mayo cart tray having an outer edge of the mayo cart tray which is not adjacent to the vertical support pole, the system comprising:
    a support apparatus for attaching to the mayo cart, to support a detachably mounted container, bracket or holder, the support apparatus having an arm extended from the vertical support pole of the mayo cart to the outer edge of the mayo cart tray, with a first attachment portion to attach to a detachable container, bracket or holder proximate a first end and opposite an end attached to the vertical support pole of the mayo cart; and
    a portion of a detachable container assembly, the detachable container assembly portion having an attachment portion to receive the first attachment portion of the support apparatus.

15. The system of claim 14, the detachable container assembly to hold medical sharps.

16. The apparatus of claim 14, the detachable container assembly to hold a liquid nitrogen dispenser.

17. The system of claim 14, the support apparatus arm operatively extended to an adjustable length.

18. The system of claim 17, the support apparatus having a second portion attachable with a securing mechanisms to secure the support apparatus to the vertical support pole.

* * * * *